United States Patent
Furuta et al.

(10) Patent No.: US 11,255,812 B2
(45) Date of Patent: Feb. 22, 2022

(54) GAS SENSOR ELEMENT, HEATER AND GAS SENSOR

(71) Applicant: NGK SPARK PLUG CO., LTD., Nagoya (JP)

(72) Inventors: Hitoshi Furuta, Tajimi (JP); Tetsuo Yamada, Komaki (JP); Yoshihiro Nakano, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 400 days.

(21) Appl. No.: 16/364,949

(22) Filed: Mar. 26, 2019

(65) Prior Publication Data

US 2019/0302050 A1    Oct. 3, 2019

(30) Foreign Application Priority Data

Mar. 27, 2018 (JP) .............................. JP2018-059397
Apr. 20, 2018 (JP) .............................. JP2018-081191
Jan. 8, 2019 (JP) .............................. JP2019-001248

(51) Int. Cl.
*G01N 27/406* (2006.01)
*F01N 3/20* (2006.01)
*G01N 33/00* (2006.01)
*G01N 27/407* (2006.01)

(52) U.S. Cl.
CPC ......... *G01N 27/4067* (2013.01); *F01N 3/208* (2013.01); *G01N 27/4076* (2013.01); *G01N 27/4077* (2013.01); *G01N 33/0037* (2013.01); *G01N 33/0054* (2013.01); *G01N 33/0073* (2013.01); *F01N 2560/021* (2013.01); *F01N 2560/026* (2013.01); *F01N 2570/16* (2013.01); *F01N 2570/18* (2013.01)

(58) Field of Classification Search
None
See application file for complete search history.

(56) References Cited

U.S. PATENT DOCUMENTS

2009/0014331 A1\* 1/2009 Sugaya .............. G01N 27/4075
                                                            204/427

FOREIGN PATENT DOCUMENTS

JP           2013-221931 A      10/2013

OTHER PUBLICATIONS

Webpage: Esslinger.com; https://blog.essling.com/metal-melting-point-chart; accessed on (Year: Jun. 24, 2021).\*

\* cited by examiner

*Primary Examiner* — J. Christopher Ball
(74) *Attorney, Agent, or Firm* — Sughrue Mion, PLLC

(57) ABSTRACT

Disclosed is a gas sensor element having an electrode containing a first metal as a predominant component and a lead containing a second metal as a predominant component. The electrode and the lead are connected directly at a connection boundary thereof, or connected indirectly via a connection joint. The connection boundary or joint includes a component region where either one of the first and second metals lower in specific gravity than the other of the first and second metals is contained in an amount ranging between those in the electrode and the lead.

10 Claims, 8 Drawing Sheets

GAS SENSOR ELEMENT, HEATER AND GAS SENSOR

FIELD OF THE INVENTION

The present invention relates to a gas sensor element, a heater and a gas sensor.

BACKGROUND OF THE INVENTION

In recent years, various sensors have been developed. For example, Japanese Laid-Open Patent Publication No. 2013-221931 discloses a gas sensor with a sensor element for measuring the concentration of ammonia in an exhaust gas of an internal combustion engine such as diesel engine. In this gas sensor, the sensor element has a structure in which electrodes are respectively connected to electrode leads. The connection section of the electrode and the electrode lead is formed by overlappingly applying a paste for the electrode and a paste for the electrode lead and firing the overlappingly applied pastes.

SUMMARY OF THE INVENTION

There is however the possibility that voids occur in e.g. a part of the electrode due to metal migration from the electrode to the electrode lead during the firing. The occurrence of such voids becomes a cause of a break in the electrode.

Depending on the kind of the sensor element, the sensor element has a heater in which a heating portion is connected to heater leads. The connection section of the heating portion and the heater lead is formed in the same manner as above by overlappingly applying a paste for the heating portion and a paste for the heater lead and firing the overlappingly applied pastes. There is also a possibility that voids occurs in e.g. a part of the heating portion due to metal migration from the heating portion to the heater lead during the firing. The occurrence of such voids becomes a cause of a break in the heater.

The present invention has been made in view the above circumstances. It is an object of the present invention to suppress a break in an electrode or lead of a gas sensor element and to suppress a break in a heating portion or lead of a heater.

The present invention can be embodied in the following aspects.

In accordance with a first aspect of the present invention, there is provided a gas sensor element, comprising: an electrode containing a first metal as a predominant component; and a lead containing a second metal as a predominant component, the electrode and the lead being connected to each other directly or indirectly via a connection joint, wherein, when the electrode and the lead are directly connected to each other, a connection boundary of the electrode and the lead includes a component region in which either one of the first and second metals lower in specific gravity than the other of the first and second metals is contained in an amount ranging between an amount of the one of the first and second metals contained in a part of the electrode other than the connection boundary and an amount of the one of the first and second metals contained in a part of the lead other than the connection boundary, and wherein, when the electrode and the lead are connected indirectly via the connection joint, the connection joint includes a component region in which either one of the first and second metals lower in specific gravity than the other of the first and second metals is contained in an amount ranging between an amount of the one of the first and second metals contained in the electrode and an amount of the one of the first and second metals contained in the lead.

When a paste for formation of the electrode and a paste for formation of the lead are subjected to heat treatment in a direct contact state, there locally occurs a contact of liquid metals of different densities. In this liquid contact area, metal migration takes place so as to relieve an abrupt difference in metal density (i.e. abrupt gradient in metal concentration). In particular, the low specific gravity metal tends to migrate toward the high specific gravity metal side. It is likely that voids will occur due to such metal migration, which can cause a break in the electrode or lead.

In the first aspect, the component region is provided to relieve the concentration gradient of one of the first and second metals lower in specific gravity (hereinafter also referred to as "lower specific gravity metal") between the electrode and the lead, whereby voids are unlikely to occur due to abrupt metal migration. It is therefore possible to suppress a break in the electrode or lead.

In accordance with a second aspect of the present invention, there is provided a gas sensor element as described above, wherein the electrode and the lead are connected indirectly via the connection joint, and wherein the other of the first and second metals is contained in the component region in an amount ranging between an amount of the other of the first and second metals contained in the electrode and an amount of the other of the first and second metals contained in the lead.

In the second aspect, the first and second metals are contained in the component region at middle concentrations between those in the electrode and the lead. By this component region, the concentration gradient of both the first and second metals is relieved to prevent the occurrence of voids due to rapid metal migration. It is thus possible to effectively suppress a break in each of the electrode and the lead.

In accordance with a third aspect of the present invention, there is provided a gas sensor element as described above, further comprising: a second electrode different from the electrode; and a solid electrolyte body arranged between the electrode and the second electrode, wherein the second electrode contains the second metal as a predominant component, and wherein the gas sensor element is configured as a mixed-potential-type sensor element.

In the case of the mixed-potential-type sensor element in which the electrode and the second electrode contain dissimilar (different) metal species as their respective predominant components and show different reactivity toward a gas under measurement, either one of these two electrodes needs to be formed of metal species dissimilar to that of the lead connected thereto. In this dissimilar metal connection section, it is likely that voids will occur due to an abrupt metal concentration gradient, which can cause a break.

In the third aspect, however, the component region is provided to relieve the abrupt metal concentration in the dissimilar metal connection section. It is thus possible to particularly effectively prevent the occurrence of voids due to metal migration and suppress a break in the electrode or lead.

In accordance with a fourth aspect of the present invention, there is provided a gas sensor element as described above, wherein metal elements of the connection joint substantially consist of the first and second metals.

Even when any metal element other than the first and second metals is contained in the connection joint, the other metal element makes no contribution to relieving the metal concentration gradient between the electrode and the lead.

In the fourth aspect, the connection joint contains, as its metal elements, substantially only the first and second metals which contribute to relieving the metal concentration gradient between the electrode and the lead. It is thus possible to obtain a high effect of relieving abrupt metal concentration gradient and suppressing metal migration.

In accordance with a fifth aspect of the present invention, there is provided a gas sensor element as described above, wherein the connection joint contains 30 to 70 mass % of the first metal and 30 to 70 mass % of the second metal based on 100 mass % of the total amount of the first and second metals.

In the fifth aspect, the connection joint contains the first and second metals at the above specific concentrations. It is thus possible to obtain a high effect of relieving abrupt metal concentration gradient and suppressing metal migration.

In accordance with a sixth aspect of the present invention, there is provided a gas sensor element as described above, wherein the electrode and the lead are directly connected to each other, with the lead being partially disposed on and overlapping the electrode, wherein the gas sensor element includes: an individual electrode section in which the electrode is present without being overlapped by the lead; a connection section in which the lead overlaps the electrode; and an individual lead section in which the electrode is present without overlapping the electrode, wherein a thickness of the connection section is larger than a sum of a thickness of the individual electrode section and a thickness of the individual lead section, and wherein, when the connection section is observed in cross section, the connection boundary is provided as a part of the connection section excluding an outer surface part of the connection section by an amount of the thickness of the individual lead section and excluding an inner surface part of the connection section by an amount of the thickness of the individual electrode section.

In the sixth aspect, the thickness of the connection section is set larger than the sum of the thickness of the individual electrode section (i.e. the thickness of the electrode itself) and the thickness of the individual lead section (i.e. the thickness of the lead itself).

Conventionally, the electrode and the lead are directly connected to each other without satisfying the above thickness relationship. In this conventional connection structure, the connection boundary is not provided with a sufficient thickness and hence allows migration of e.g. the first metal migrates from the electrode function part to the lead function part so that there is the possibility of a break in the connection section due to such metal migration.

In the sixth aspect, the connection boundary is provided with a sufficient thickness, as the part of the connection section, to limit migration of the lower specific gravity metal to within the connection boundary. As the lower specific gravity metal is prevented from migration from the electrode function part to the lead 16 function part (or from the lead function part to the electrode function part) of the connection section, it is possible to effectively suppress a break in the connection section.

In accordance with a seventh aspect of the present invention, there is provided a gas sensor element as described above, wherein the electrode and the lead are directly connected to each other, with the electrode being partially disposed on and overlapping the lead, wherein the gas sensor element includes: an individual electrode section in which the electrode is present without overlapping the lead; a connection section in which the electrode overlaps the lead; and an individual lead section in which the lead is present without being overlapped by the electrode, wherein a thickness of the connection section is larger than a sum of a thickness of the individual electrode section and a thickness of the individual lead section, and wherein, when the connection section is observed in cross section, the connection boundary is provided as a part of the connection section excluding an outer surface part of the connection section by an amount of the thickness of the individual electrode section and excluding an inner surface part of the connection section by an amount of the thickness of the individual lead section.

In the seventh aspect, the thickness of the connection section is set larger than the sum of the thickness of the individual electrode section and the thickness of the individual lead section.

Conventionally, the electrode and the lead are directly connected to each other without satisfying the above thickness relationship as mentioned above. In this conventional connection structure, the connection boundary is not provided with a sufficient thickness and hence allows migration of e.g. the first metal from the electrode function part to the lead function part of the connection section so that there is the possibility of a break in the connection section due to such metal migration.

In the seventh aspect, the connection boundary is provided with a sufficient thickness, as the part of the connection section, to limit migration of the lower specific gravity metal to within the connection boundary. As the lower specific gravity metal is prevented from migration from the electrode function part to the lead function part (or from the lead function part to the electrode function part) of the connection section, it is possible to effectively suppress a break in the connection section.

In accordance with an eighth aspect of the present invention, there is provided a gas sensor element as described above, wherein the specific gravity of the first metal is lower than the specific gravity of the second metal.

In the eighth aspect, the first metal is prevented by the component region from migration during the firing. It is thus possible to effectively suppress a break in the electrode.

In accordance with a ninth aspect of the present invention, there is provided a gas sensor element as described above, wherein the first metal is gold, and wherein the second metal is platinum.

In the case of using gold and platinum in combination, there is a high tendency that the migration of gold will take place during the firing.

In the ninth aspect, however, such metal migration is prevented by the component region. It is thus possible to effectively suppress a break in the electrode.

In accordance with a tenth aspect of the present invention, there is provided a gas sensor element as described above, wherein the gas sensor element is configured to measure a concentration of ammonia in a gas under measurement.

In the tenth aspect, the gas sensor element is configured as an ammonia sensor element. In this case, it is possible to obtain a high effect of relieving abrupt metal concentration gradient, suppressing metal migration during heat treatment and preventing voids which become a cause of a break.

In accordance with an eleventh aspect of the present invention, there is provided a heater, comprising: a heating portion containing a first metal as a predominant component; and a lead containing a second metal as a predominant component, the heating portion and the lead being connected to each other directly or indirectly via a connection joint, wherein, when the heating portion and the lead are directly connected to each other, a connection boundary of the heating portion and the lead includes a component region in which either one of the first and second metals lower in specific gravity than the other of the first and second metals is contained in an amount ranging between an amount of the one of the first and second metals contained in a part of the heating portion other than the connection boundary and an amount of the one of the first and second metals contained in a part of the lead other than the connection boundary; and wherein, when the heating portion and the lead are connected indirectly via the connection joint, the connection joint includes a component region in which either one of the first and second metals lower in specific gravity than the other of the first and second metals is contained in an amount ranging between an amount of the one of the first and second metals contained in the heating portion and an amount of the one of the first and second metals contained in the lead.

In the eleventh aspect, the component region is provided to relieve the concentration gradient of one of the first and second metals lower in specific gravity (referred to as "lower specific gravity metal") between the heating portion and the lead, whereby metal migration is suppressed. As voids are unlikely to occur due to metal migration, it is possible to suppress a break in the heating portion or lead.

In accordance with a twelfth aspect of the present invention, there is provided a gas sensor comprising the above gas sensor element or the above heater.

In this gas sensor, it is possible to relieve the abrupt metal concentration gradient between the electrode and the lead or between the heating portion and the lead, suppress metal migration during heat treatment such as firing and thereby prevent the occurrence of voids which become a cause of a break in the electrode, heating portion or lead.

The other objects and features of the present invention will also become understood from the following description.

DESCRIPTION OF EMBODIMENTS

First Embodiment

A multi-gas sensor apparatus 1 with an ammonia sensor unit 21 according to the first embodiment of the present invention will be described below with reference to FIGS. 1 to 4.

In the first embodiment, the multi-gas sensor apparatus 1 is designed for use in a urea selective catalytic reduction (SCR) system, which purifies nitrogen oxides (NOx) in an exhaust gas of an internal combustion engine, and is configured to measure the concentrations of nitrogen monoxide (NO), nitrogen dioxide ($NO_2$) and ammonia in the exhaust gas (as a gas under measurement) after reaction of NOx with ammonia (urea) in the urea SCR system. There is no particular limitation on the engine to which the multi-gas sensor apparatus 1 is applied. The engine can be a diesel engine or a gasoline engine.

Figure 1:
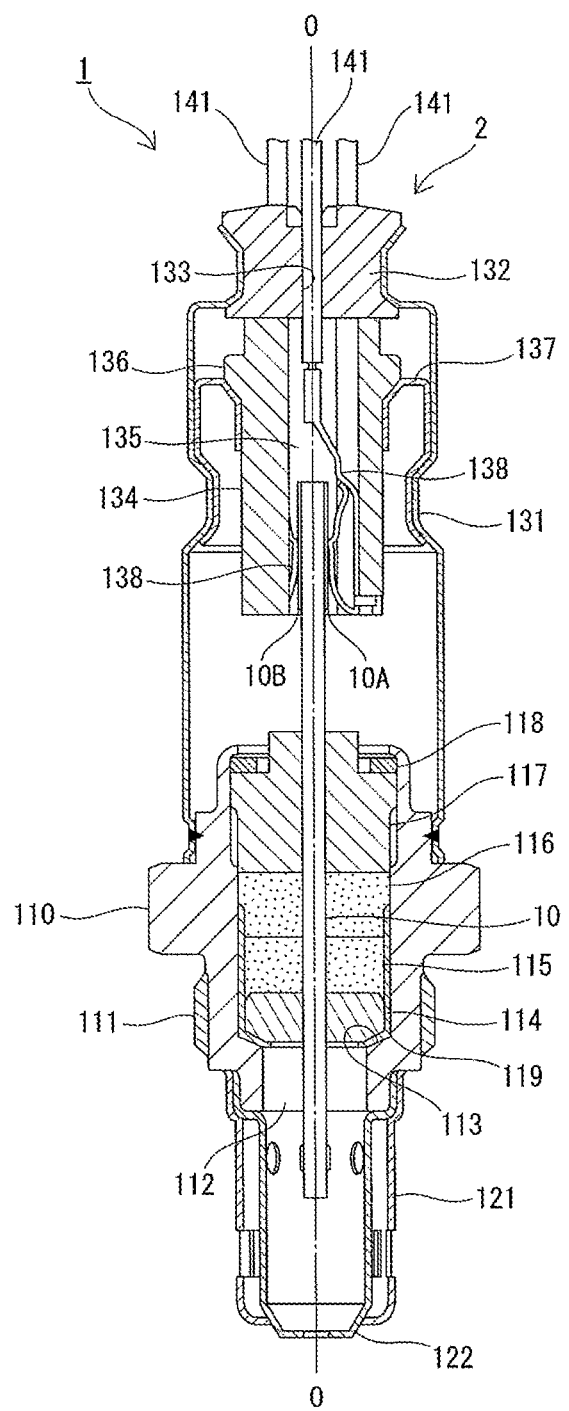
FIG. 1 is a cross-sectional view of a multi-gas sensor according to a first embodiment of the present invention.
Figure 2:
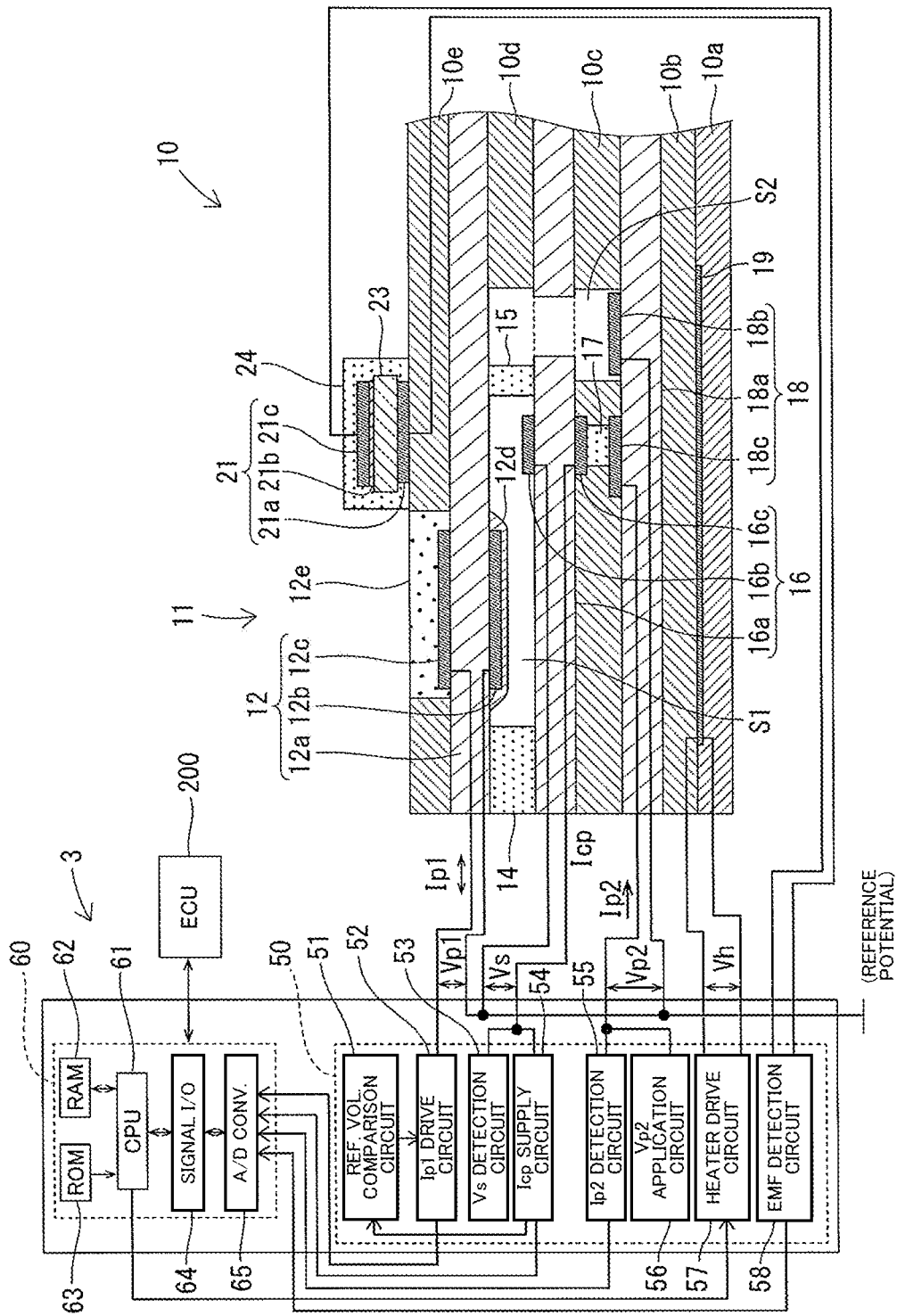
FIG. 2 is a block diagram of a multi-gas sensor apparatus with the multi-gas sensor according to the first embodiment of the present invention.

As shown in FIGS. 1 and 2, the multi-gas sensor apparatus 1 includes a multi-gas sensor 2 as a sensor body and a sensor controller 3 that controls operations of the multi-gas sensor 2 and determines the NO, $NO_2$ and ammonia concentrations by processing of outputs of the multi-gas sensor 2.

The multi-gas sensor 2 has a sensor element assembly 10, a metal shell 110, a separator 134 and connection terminals 138 as shown in FIG. 1.

In the following description, the term "front" refers to a side of the multi-gas sensor 2 on which the sensor element assembly 10 is disposed (i.e. a bottom side of FIG. 1); and the term "rear" refers to a side of the multi-gas sensor 2 on which the connection terminals 138 are disposed (i.e. a top side of FIG. 1).

The sensor element assembly 10 is plate-shaped, extending in the direction of an axis O of the multi-gas sensor 2. Electrode terminals 10A and 10B are arranged on a rear end part of the sensor element assembly 10. Although two electrode terminals 10A and 10B are representatively shown in FIG. 1 for simplification purposes, there are in fact provided a plurality of electrode terminals corresponding to the number of electrodes of the after-mentioned NOx and ammonia sensor units 21 of the multi-gas sensor 2. A detailed explanation of the sensor element assembly 10 will be given later.

The metal shell 110 is cylindrical-shaped, having a through hole 112 formed therethrough in the direction of the axis O. The metal shell 110 includes: a thread portion 111 formed on an outer circumferential surface thereof to mount the multi-gas sensor 2 to an exhaust pipe of the engine; and a shelf portion 113 radially inwardly protruding in the through hole 112 and having an inward taper surface tapering down toward the front.

The sensor element assembly 10 is held in the though hole 112 of the metal shell 110, with a front end portion of the sensor element assembly 10 being exposed frontward from the through hole 112 and a rear end portion of the sensor element assembly 10 being exposed rearward from the through hole 112.

An annular ceramic holder 114, annular filled layers 115 and 116 of talc powder (hereinafter referred to as "talc rings 115 and 116") and an annular ceramic sleeve 117 are arranged in the through hole 112 of the metal shell 110 so as to circumferentially surround the sensor element assembly 10. A crimp packing 118 is arranged between the ceramic sleeve 117 and a rear end portion of the metal shell 110. The rear end portion of the metal shell 110 is crimped to push the ceramic sleeve 117 toward the front via the crimp packing 118. A metal holder 119 is arranged between the ceramic holder 114 and the shelf portion 113 of the metal shell 110 so as to hold the talc ring 115 and the ceramic holder 114.

A double-structure protector with outer and inner protector members 121 and 122 is fixed to a front end portion of the metal shell 110. Each of the outer and inner protector members 121 and 122 is cylindrical-shaped, with a front end thereof closed, and is made of a metal material such as stainless steel. The inner protector member 122 is welded to the front end portion of the metal shell 110 so that the exposed front end portion of the sensor element assembly 10 is covered with the inner protector member 122. The outer protector member 121 is welded to the front end portion of the metal shell 110 so that the inner protector member 122 is covered with the outer protector member 121.

A cylindrical outer tube 131 is fixed at a front end portion thereof to the rear end portion of the metal shell 111. A grommet 132 is fitted in a rear end portion of the outer tube 131 so as to close an opening of the rear end portion of the outer tube 131. Lead insertion holes 133 are formed through the grommet 132. Leads 141 are inserted through the lead insertion holes 133 and electrically connected to the electrode terminals 10A and 10B on the sensor element assembly 10.

The separator 134 is cylindrical-shaped, having an insertion hole 135 formed therethrough in the direction of the axis O. The separator 134 includes a collar portion 136 radially outwardly protruding from an outer circumferential surface thereof. The separator 134 is disposed on a rear end side of the sensor element assembly 10 in the outer tube 131 so that the rear end portion of the sensor element assembly 10 is inserted in the insertion hole 135 of the separator 134, with the electrode terminals 10A and 10B being situated inside the separator 134.

A cylindrical retaining member 137 is arranged between the separator 134 and the outer tube 131 so as to retain and fix the separator 134 in the outer tube 131 by contact of the retaining member 137 with the collar portion 136 of the separator 134 and the inner surface of the outer tube 131.

The connection terminals 138 are arranged in the insertion hole 135 of the separator 134 so as to establish electrical connection of the leads 141 to the electrode terminals 10A and 10B on the sensor element assembly 10. In FIG. 1, only two connection terminals 138 are representatively shown for simplification purposes.

As shown in FIG. 2, the sensor controller 3 is electrically connected to an ECU 200 (as a vehicle-side controller) of a vehicle on which the multi-gas sensor apparatus 1 is mounted. Herein, the ECU 200 is configured to receive data on the determined NO, $NO_2$ and ammonia concentration of the exhaust gas from the sensor controller 3 and performs various control processing such as drive control of the engine and purification treatment of NOx accumulated in the catalyst of the SCR system based on the received data.

The configuration of the sensor element assembly 10 will be explained in detail below with reference to FIGS. 2 to 4. For convenience of explanation, the sensor element assembly 10 is shown in cross section along its longitudinal direction in FIG. 2.

The sensor element assembly 10 has a NOx sensor unit 11 (as a NOx detection element) and an ammonia sensor unit 21. In the first embodiment, the ammonia sensor unit 21 corresponds to the claimed gas sensor element.

In the first embodiment, the NOx sensor unit 11 is of the same structure as that of a known NOx sensor. More specifically, the NOx sensor unit 11 has a structure in which an insulating layer 10e, a first solid electrolyte body 12a, an insulating layer 10d, a third solid electrolyte body 16a, an insulating layer 10c, a second solid electrolyte body 18a and insulating layers 10b and 10a are stacked together in this order. The insulating layers 10a, 10b, 10c, 10d and 10e are each predominantly made of alumina. There is a first measurement chamber S1 defined between the first solid electrolyte body 12a and the third solid electrolyte body 16a. There is a second measurement chamber S2 (as a NOx measurement chamber) defined between the first solid electrolyte body 12a and the second solid electrolyte body 18a through the third solid electrolyte body 16a.

A first diffusion limiting member 14 is arranged at an inlet-side end (left-side end in FIG. 2) of the first measurement chamber S1. A second diffusion limiting member 15 is arranged at an outlet-side end of the first measurement chamber S1 (opposite from the inlet-side end) so as to serve as a partition between the first and second measurement chambers S1 and S2. The first and second diffusion limiting members 14 and 15 are each made of a porous material such as alumina to allow permeation of the gas under measurement.

In the NOx sensor unit 11I, a heater 19 is arranged to heat the NOx sensor unit 11 and the ammonia sensor unit 21 to activation temperatures and enhance the oxygen ion conductivity of the solid electrolyte bodies of these sensor units 11 and 21. The heater 19 has a heating portion made of platinum or platinum alloy in an elongated shape along the longitudinal direction of the sensor element assembly 10 and embedded between the insulating layers 10b and 10a.

The first solid electrolyte body 12a is predominantly made of oxygen-ion-conductive zirconia and is sandwiched between an inner first pumping electrode 12b and an outer first pumping electrode 12c (as a counter electrode). Herein, the first solid electrolyte body 12a and the first pumping electrodes 12b and 12c constitute a first pumping cell 12. The inner and outer first pumping electrodes 12b and 12c are each predominantly made of platinum. The inner first pumping electrode 12b is arranged on a surface of the first solid electrolyte body 12a exposed to the first measurement chamber S1. A first measurement chamber S1-side surface of the inner first pumping electrode 12b is covered with a protection layer 12d of porous material. The outer first pumping electrode 12c is arranged in a hollow part of the insulating layer 10e at a position opposed to the inner first pumping electrode 12b via the solid electrolyte layer 12a. This hollow part is filled with a porous material 12e so as to allow a flow of gas (oxygen) between the outer first pumping electrode 12c and the outside.

The third solid electrolyte body 16a is predominantly made of zirconia and is sandwiched between a detection electrode 16b and a reference electrode 16c (as a counter electrode). Herein, the third solid electrolyte body 16a, the detection electrode 16b and the reference electrode 16c constitute an oxygen concentration detection cell 16. The detection electrode 16b and the reference electrode 16c are each predominantly made of platinum. The detection electrode 16b is arranged on a surface of the third solid electrolyte body 16a exposed to the first measurement chamber S1 at a position downstream of the inner first pumping electrode 12b, that is, close to the second diffusion limiting member 15. The reference electrode 16c is arranged in a hollow part of the insulating layer 10c. This hollow part is formed as a reference oxygen chamber 17 and is filled with a porous material. Into the reference oxygen chamber 17, oxygen is pumped from the first measurement chamber S1 as reference oxygen.

The second solid electrolyte body 18a is predominantly made of zirconia. An inner second pumping electrode 18b and a second pumping counter electrode 18c, each of which is predominantly made of platinum, are disposed on a second measurement chamber S2-side surface of the second solid electrolyte body 18a. Herein, the second solid electrolyte body 18a and the second pumping electrodes 18b and 18c constitute a second pumping cell 18. The inner second pumping electrode 18b is arranged on a part of the second solid electrolyte body 18a exposed to the second measurement chamber S2. The second pumping counter electrode 18c is arranged on a part of the second solid electrolyte body 18a exposed to the reference oxygen chamber 17 and opposed to the reference electrode 16c.

The inner first pumping electrode 12b, the detection electrode 16b and the inner second pumping electrode 18b are each connected to a reference potential.

On the other hand, the ammonia sensor unit 21 is located on an outer surface of the NOx sensor unit 11 (more specifically, on the insulating layer 10e) at substantially the same position as the reference electrode 16c of the NOx sensor unit 11 in the direction of the axis O. In the first embodiment, the ammonia sensor unit 21 is provided at such a position that the temperature of the outer surface of the NOx sensor unit 11 becomes 650° C. when the control temperature of the second solid electrolyte body 18a of the NOx sensor unit 11 is set to 600° C.

Figure 3:
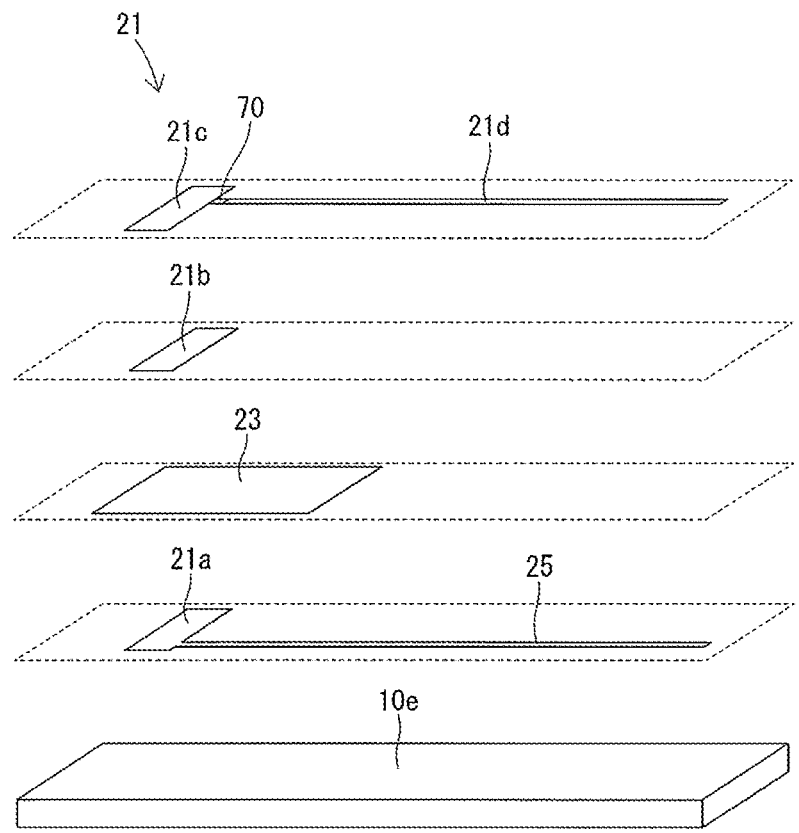
FIG. 3 is an exploded perspective view of an ammonia sensor unit of the multi-gas sensor according to the first embodiment of the present invention.

As shown in FIGS. 2 and 3, the ammonia sensor unit 21 is of the mixed potential type having a structure in which a reference electrode 21a, a solid electrolyte body 23, an intermediate layer 21b (as an electrode) and an ammonia detection electrode 21c are stacked together in this order. Herein, the ammonia detection electrode 21c corresponds to the claimed electrode; the ammonia detection electrode lead 21d corresponds to the claimed lead; the reference electrode 21a corresponds to the claimed second electrode; and the solid electrolyte body 23 corresponds to the claimed solid electrolyte body. The ammonia sensor unit 21 is integrally covered with a protection layer 24 of porous material.

More specifically, the reference electrode 21a is rectangular-shaped and disposed on an outer surface of the insulating layer 10e. The reference electrode 21a is made of a material containing platinum (Pt) as a predominant component. In other words, the reference electrode 21a is made of Pt alone or Pt-based alloy. The reference electrode 21a is so adapted that a combustible gas is burned at a surface of the reference electrode 21a.

A reference electrode lead 25, which is made predominantly of platinum (Pt), is connected to the reference electrode 21a and arranged on the insulating layer 10e so as to extend in the longitudinal direction (horizontal direction in FIG. 3; that is, the direction of the axis O). A rear end part (right-side end in FIG. 3) of the reference electrode lead 25 is formed as an electrode terminal.

The solid electrolyte body 23 is disposed on an outer surface of the reference electrode 21a such that the reference electrode 21a is sandwiched between the solid electrolyte body 23 and the insulating layer 10e. The solid electrolyte body 23 is made predominantly of an oxygen-ion-conductive solid electrolyte material such as yttria-stabilized zirconia (YSZ).

The intermediate layer 21b is disposed on an outer surface of the solid electrolyte body 23 at a position opposed to the reference electrode 21a. The intermediate layer 21b is made of a material containing 50 mass % or more of an oxygen-ion-conductive solid electrolyte material such as zirconia together with an oxide of at least one kind of metal selected from the group consisting of cobalt (Co), manganese (Mn), copper (Cu), nickel (Ni) and cerium (Ce) as a first metal oxide. In the first embodiment, the intermediate layer 21b is made predominantly of cobalt oxide ($Co_3O_4$) and zirconia. When cobalt oxide ($Co_3O_4$) is contained as the first metal oxide, variations in ammonia concentration detection sensitivity of the ammonia sensor unit 21 can be suppressed by the action of $H_2O$ contained in the gas under measurement. The first metal oxide is in the form of a metal oxide or a composite oxide. The solid electrolyte material contained in the intermediate layer 21b can be of the same kind as or a different kind from those used in the multi-gas sensor 2.

The amount of the first metal oxide contained in the intermediate layer 21b is preferably in the range of 1 mass % to 50 mass %. When the amount of the first metal oxide contained is less than 1 mass %, the intermediate layer 21b may not ensure sufficient selectivity to ammonia gas. When the amount of the first metal oxide contained exceeds 50 mass %, the amount of the solid electrolyte material contained in the intermediate layer 21b becomes decreased so that the oxygen ion conductivity of the intermediate layer 21b may be lowered.

Further, the intermediate layer 21b is preferably provided as a porous electrode layer in order to improve the ammonia gas selectivity of the intermediate layer 21b and thereby increase the ammonia concentration detection sensitivity of the ammonia sensor unit 21.

It is feasible to confirm whether or not the first metal oxide is contained in the intermediate layer 21b by analyzing a cross section of the ammonia sensor unit 21 with an electron probe micro analyzer (EPMA). In general, the presence of the first metal oxide in the intermediate layer 21b can be confirmed based on the average of results of EPMA analysis performed at three points on the cross section.

The ammonia detection electrode 21c is disposed on an outer surface of the intermediate layer 21b such that the solid electrolyte body 23 and the intermediate layer 21b are sandwiched between the ammonia detection electrode 21c and the reference electrode 21a.

An ammonia detection electrode lead 21d is connected to the ammonia detection electrode 21c and arranged to extend from the ammonia detection electrode 21c in the longitudinal direction. As shown in FIG. 4, the ammonia detection electrode 21c and the ammonia detection electrode lead 21d are electrically connected to each other via a joint 70 in the first embodiment. This joint 70 corresponds to the claimed connection joint (component region) as will be explained in detail later. A rear end part of the ammonia detection electrode lead 21d is formed as an electrode terminal.

The ammonia detection electrode 21c is made of a material containing a first metal as a predominant component; whereas the ammonia detection electrode lead 21d is made of a component containing a second metal as a predominant component. In the first embodiment, the first metal is gold (Au) and is contained in an amount of 70 mass % or more in the ammonia detection electrode 21c; and the second metal is platinum (Pt) and is contained in an amount of 50 mass % or more in the ammonia detection electrode lead 21d.

The first metal oxide is not necessarily contained in the ammonia detection electrode 21c. When the first metal oxide is not contained in the ammonia detection electrode 21c, however, combustion of ammonia gas on the ammonia detection electrode 21c can be suppressed so that the amount of ammonia gas reaching the interface between the ammonia detection electrode 21c and the intermediate layer 21b becomes unlikely to decrease. In other words, the detection accuracy of the ammonia sensor unit 21 can be improved so as to enable accurate detection of low-concentration ammonia (e.g. of the order of 10 ppm).

Since Au is contained in the ammonia detection electrode 21c in an amount of 70 mass % or more, the ammonia detection electrode 21c ensures its function as a collector. When the ammonia detection electrode 21c is made of a material containing less than 70 mass % of Au, it becomes difficult to ensure the collector function of the ammonia detection electrode 21c, that is, difficult to detect ammonia gas by the ammonia sensor unit 21.

Preferably, the ammonia detection electrode 21c is provided as a porous electrode containing, as a second metal oxide, an oxide of at least one kind of metal selected from the group consisting of zirconium (Zr), yttrium (Y), aluminum (Al) and silicon (Si) in order to impart gas permeability to the ammonia detection electrode 21c. In this case, ammonia gas easily passes through the ammonia detection electrode 21c and reaches the interface between the ammonia detection electrode 21c and the intermediate layer 21b. The amount of the second metal oxide contained in the ammonia detection electrode 21c is preferably in the range of 5 mass % to 30 mass %.

The ammonia gas reaching the interface between the ammonia detection electrode 21c and the intermediate layer 21b undergoes reaction (electrode reaction) with oxygen ions at this interface. Accordingly, the ammonia detection electrode 21c serves as a detector of ammonia gas. When the first metal oxide is present at the interface between the ammonia detection electrode 21c and the intermediate layer 21b, the ammonia gas selectivity of the ammonia detection electrode 21c and the intermediate layer 21b is improved with decrease in the sensitivity of the ammonia detection electrode 21c and the intermediate layer 21b to any gas other than ammonia gas (such as HC gas).

The reason for such improvement in ammonia gas selectivity is not clear, but is assumed to be that: the field of electrode reaction is modified by the first metal oxide present at the interface between the ammonia detection electrode 21c and the intermediate layer 21b; and, as the first metal oxide is acidic and strongly interacts with basic ammonia ($NH_3$), the electrode reaction of ammonia gas proceeds preferentially over reaction of any other gas.

Although the ammonia detection electrode 21c and the intermediate layer 21b are separately provided in the first embodiment, it is alternatively feasible contain the first metal oxide (cobalt oxide) in the ammonia detection electrode 21c and omit the intermediate layer 21b.

The protection layer 24 is formed to prevent adhesion of a poisoning substance to the ammonia detection electrode 21c and to adjust the rate of diffusion of the gas under measurement from the outside into the ammonia sensor unit 21. As the material of the protection layer 24, there can be used at least one kind selected from the group consisting of alumina (aluminum oxide), spinel ($MgAl_2O_4$), silica alumina and mullite. The rate of diffusion of the gas under measurement through the protection layer 24 can be adjusted by varying the thickness, particle size, particle distribution, porosity, material mixing ratio etc. of the protection layer 24.

Although the ammonia sensor unit 21 is covered with the protection layer 24 in the first embodiment, the ammonia sensor unit 21 is not limited to such configuration. The ammonia detection electrode 21c may alternatively be exposed with no protection layer formed.

As shown in FIG. 2, the sensor controller 3 has, mounted on a circuit board, an analog control circuit module 50 and a microcomputer 60.

The microcomputer 60 is configured to control the whole of the sensor controller 3. Generally, the microcomputer 60 is provided with a CPU (central processing unit) 61, a storage unit including a RAM 62 and a ROM 63, a signal input/output part 64, a A/D converter 65, a clock (not shown) and the like so as to perform processing operation with the execution of various programs stored in the ROM 63 etc. by the CPU 61.

The control circuit module 50 is configured to control operation of the multi-gas sensor 2 and output detection values of the multi-gas sensor 2 to the microcomputer 60. The control circuit module 50 is provided with a reference voltage comparison circuit 51, a IP1 drive circuit 52, a Vs detection circuit 53, a Icp supply circuit 54, a Ip2 detection circuit 55, a Vp2 application circuit 56, a heater drive circuit 57 and an electromotive force detection circuit 58. The Ip1 drive circuit 52 is electrically connected to the outer first pumping electrode 12c of the NOx sensor unit 11. The Vs detection circuit 53 and the Icp supply circuit 54 are electrically connected in parallel to the reference electrode 16c of the NOx sensor unit 11. The Ip detection circuit 55 and the Vp2 application circuit 56 are electrically connected in parallel to the second pumping counter electrode 18c of the NOx sensor unit 11. The heater drive circuit 57 is electrically connected to the heater 19 of the NOx sensor unit 11. The electromotive force detection circuit 58 is electrically connected to the reference electrode 21a and ammonia detection electrode 21c of the ammonia sensor unit 21.

The electromotive force detection circuit 58 detects an electromotive force (EMF) between the reference electrode 21a and the ammonia detection electrode 21c as an ammonia concentration output value and outputs the detected ammonia electromotive force to the microcomputer 60.

The Ip1 drive circuit 52 supplies a first pumping current Ip1 between the inner and outer first pumping electrodes 12b and 12c while detecting and controlling the first pumping current Ip1. Further, the Ip1 drive circuit 52 outputs the detected first pumping current Ip1 to the A/D converter 65.

The Vs detection circuit 53 detects a voltage Vs between the detection electrode 16b and the reference electrode 16c and outputs the detected voltage Vs to the reference voltage comparison circuit 51. The reference voltage comparison circuit 51 compares the output voltage Vs of the Vs detection circuit 53 with a reference voltage (e.g. 425 mV) and outputs the comparison result to the Ip1 drive circuit 52. Based on the comparison result, the direction and magnitude of the first pumping current Ip1 are controlled by the Ip1 drive circuit 52 so as to set the voltage Vs equal to the reference voltage and adjust the concentration of oxygen in the first measurement chamber S1 to a predetermined level at which the decomposition of NOx does not occur.

The Icp supply circuit 54 supplies a small current Icp between the detection electrode 16b and the reference electrode 16c. By the supply of the current Icp, oxygen is pumped from the first measurement chamber S1 to the reference oxygen chamber 17 so that the reference electrode 6c is exposed to a predetermined reference oxygen concentration.

The Vp2 application circuit 56 applies a constant voltage Vp2 (e.g. 450 mV) between the inner second pumping electrode 18b and the second pumping counter electrode 18c whereby NOx in the gas under measurement is decomposed into oxygen gas ($O_2$) and nitrogen gas ($N_2$).

The Ip2 detection circuit 55 detects a second pumping current Ip2 flowing in the second pumping cell 18 at the time when $O_2$ generated by decomposition of NOx is pumped from the second measurement chamber S2 to the second pumping counter electrode 18c through the second solid electrolyte body 18a, and then, outputs the detected second pumping current Ip2 to the A/D converter 65.

The first and second pumping currents Ip1 and Ip2 are converted into digital signals by the A/D converter 65. These converted digital signals are outputted to the CPU 61 via the signal input/output part 64.

Next, a production method of the sensor element assembly 10 with the NOx sensor unit 11 and the ammonia sensor unit 21 will be explained below. As the NOx sensor unit 11 can be produced by a known method, a detail explanation of the production method of the NOx sensor unit 11 will be omitted herefrom. On the other hand, the ammonia sensor unit 21 can be produced by the following method.

First prepared is a paste containing Pt as the predominant component of the reference electrode 21a, an alumina binder (as a common inorganic oxide base material) and an organic solvent. The prepared paste (hereinafter referred to as "Pt-containing paste") is screen printed on the insulating layer 10e and fired at a predetermined temperature (e.g. about 1400° C. or higher). Further, a paste is prepared containing a powder of oxide as the predominant component of the solid electrolyte body 23, a binder and an organic solvent. The prepared solid electrolyte paste is screen printed on the fired reference electrode 21a and fired at a predetermined temperature (e.g. 1500° C.). Thus formed are the reference electrode 21a and the solid electrolyte body 23.

The intermediate layer 21b is formed on the solid electrolyte body 23 by preparing a paste containing the first metal oxide and solid electrolyte material as the components of the intermediate layer 21b, screen printing the prepared paste on the solid electrolyte body 23 and firing the printed paste at a predetermined temperature (e.g. 1000° C.).

After that, a Pt-containing paste for formation of the ammonia detection electrode lead 21d is prepared and screen printed on the intermediate layer 21b. A Pt/Au-containing paste for formation of the joint 70 is prepared and screen printed over an end part of the printed Pt-containing paste. An Au-containing paste for formation of the ammonia detection electrode 21c is prepared and screen printed on the intermediate layer 21b so as to overlap a part of the printed Pt/Au-containing paste. These overlappingly printed pastes are fired at a predetermined temperature (e.g. 1000° C.), thereby forming the ammonia detection electrode 21c in electrical connection with the ammonia detection electrode lead 21d via the joint 70. Finally, the protection layer 24 is formed by preparing a paste containing alumina etc., screen printing the prepared paste over the reference electrode 21a, the solid electrolyte body 23, the intermediate layer 21b and the ammonia detection electrode 21c, and then, firing the printed paste at a predetermined temperature (e.g. 1000° C.). With this, the ammonia sensor unit 21 is completed.

The joint 70 between the ammonia detection electrode 21c and the ammonia detection electrode lead 21d as the characteristic configuration of the first embodiment will be now explained in detailed below.

In the first embodiment, the joint 70 contains Au (as the first metal) and Pt (as the second metal) in a total amount of 50 mass % or more. The amount of Au contained in the joint 70 ranges between the amount of Au contained in the ammonia detection electrode 21c and the amount of Au contained in the ammonia detection electrode lead 21c. Namely, the concentration of Au in the joint 70 is lower than the concentration of Au in the ammonia detection electrode 21c and higher than the concentration of Au in the ammonia detection electrode lead 21d. Further, the amount of Pt contained in the joint 70 ranges between the amount of Pt contained in the ammonia detection electrode 21c and the amount of Pt contained in the ammonia detection electrode lead 21d. Namely, the concentration of Pt in the joint 70 is lower than the concentration of Pt in the ammonia detection electrode lead 21d and higher than the concentration of Pt in the ammonia detection electrode 21c. The joint 70 has a Au concentration value between those of the ammonia detection electrode 21c and the ammonia detection electrode lead 21d and has a Pt concentration value between those of the ammonia detection electrode 21c and the ammonia detection electrode lead 21d.

The amount of Au in the joint 70 is preferably 30 to 70 mass %, more preferably 40 to 60 mass %, still more preferably 45 to 55 mass %, based on 100 mass % of the total amount of Au and Pt in the joint 70.

The amount of Pt in the joint 70 is preferably 30 to 70 mass %, more preferably 40 to 60 mass %, still more preferably 45 to 55 mass %, based on 100 mass % of the total amount of Au and Pt in the joint 70.

It is preferable that metal elements of the joint 70 substantially consist of Au and Pt. The expression "substantially consist of Au and Pt" means that the amount of any metal element other than Au and Pt is substantially 0% (more specifically, less than 5.0 mass %).

In the ammonia sensor unit 21, the joint 70 is provided to relieve the abrupt metal concentration gradient between the ammonia detection electrode 21c and the ammonia detection electrode lead 21d. It is thus unlikely that Au as the predominant component of the ammonia detection electrode 21c will migrate to the ammonia detection electrode lead 21d during the firing (heat treatment) step. It is consequently possible to prevent the occurrence of voids in the ammonia detection electrode 21c due to the migration of Au and thereby possible to suppress a break in the ammonia detection electrode 21c.

In the case of using Au as the first metal in combination with Pt as the second metal, there is a high tendency that the migration of Au will take place during the firing step. Such metal migration is however effectively suppressed by the joint 70.

Second Embodiment

A gas sensor 310 according to the second embodiment of the present invention will be described below with reference to FIGS. 5 to 8.

Figure 5:
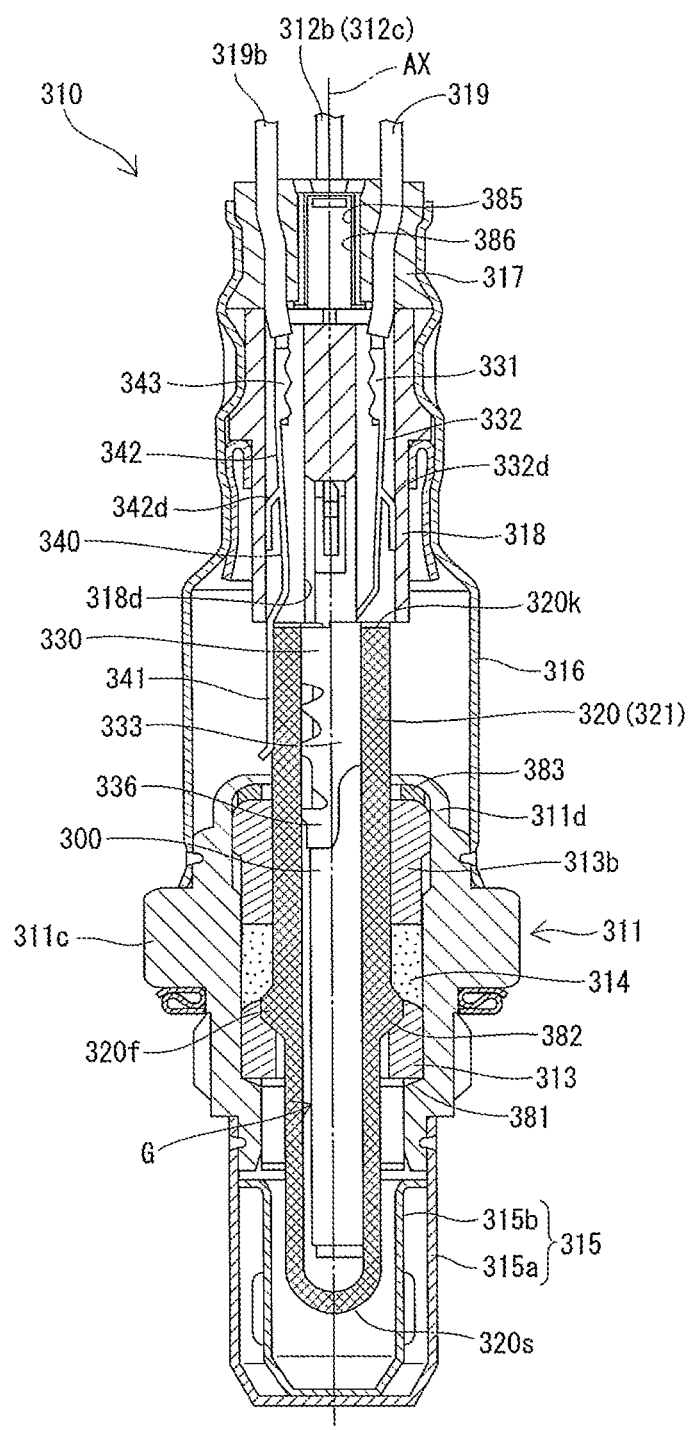
FIG. 5 is a cross-sectional view of a gas sensor with a ceramic heater according to a second embodiment of the present invention.

As shown in FIG. 5, the gas sensor 310 is provided with an oxygen detection element 320, a metal shell 311, inner and outer terminal members 330 and 340 and a ceramic heater 300. In the second embodiment, the ceramic heater 300 corresponds to the claimed heater.

In the following description, the term "front" refers to a side of the gas sensor 310 on which the heater 300 and the oxygen detection element 320 are disposed (i.e. a bottom side of FIG. 5); and the term "rear" refers to a side of the gas sensor 310 on which the terminal members 330 and 340 are disposed (i.e. a top side of FIG. 5).

The oxygen detection element 320 has a bottomed-cylindrical shape substantially U-shaped in cross section, with a front end 320s thereof closed and a rear end 320k thereof open, and extending in the direction of an axis AX of the gas sensor 310. The oxygen detection element 320 includes: an oxygen-ion-conductive solid electrolyte body 321; an outer electrode layer (not shown) formed by e.g. plating on a part of an outer circumferential surface of the solid electrolyte body 321; and an inner electrolyte layer (not shown) formed by e.g. plating on a part of an inner circumferential surface of the solid electrolyte body 321. A radially outwardly protruding engagement flange portion 320f is provided on the outer circumference of the oxygen detection element 320 at around a middle point in the direction of the axis AX.

The metal shell 311 has a cylindrical shape to surround a part of the outer circumference of the oxygen detection element 320. The oxygen detection element 320 is hermetically held in the metal shell 311 by engagement of the engagement flange portion 320f of the oxygen detection element 320 to the inner circumference of the metal shell 311 via metal packings 381, 382 and 383, insulators 313 and 313b and ceramic powder 314. As shown in FIG. 5, the metal shell 311 includes: a hexagonal portion 311c formed on an outer circumferential surface thereof; and a connection portion 311d formed rearward of the hexagonal portion 311c.

A protector 315 is fixed to the metal shell 311 so as to cover a front end portion of the oxygen detection element 320 protruding from a front end of the metal shell 311. In the second embodiment, the protector 315 has a double structure with outer and inner protector members 315a and 315b. A plurality of gas holes are formed in the outer and inner protector members 315a and 315b such that a gas under measurement (such as exhaust gas) is fed to the inside of the protector 315 through these gas holes and brought into contact with the outer electrode layer of the oxygen detection element 320.

A cylindrical outer tube 316 of metal is joined to the connection portion 311d by laser welding the entire circumference of the outer tube 316 from outside. An open rear end of the outer tube 316 is closed and sealed by fitting therein a grommet 317 of fluorocarbon rubber and swaging the rear end of the outer tube 316. A separator 318 of insulating ceramic material (such as alumina) is disposed on a front end side of the grommet 317 in the outer tube 316. Sensor output leads 319 and 319b and heater leads 312b and 312c are arranged to extend from the oxygen detection element 310 in the direction of the axis AX through lead insertion holes of the grommet 317 and a retaining hole 318d of the separator 318. A through hole is formed in the center of the grommet 317 along the direction of the axis AX. A metal pipe 386 with a water-repellent, air-permeable sheet-type filter 385 is fixed in the through hole of the grommet 317 so that the air is introduced from the outside of the gas sensor 310 into the outer tube 316 through the filter 385 and then fed to an inner space G of the oxygen detection element 320.

The outer terminal member 340 is made from a stainless steel plate, and includes: an outer fitting portion 341 substantially C-shaped in cross section in a direction perpendicular to the axis AX; a separator insertion portion 342 extending rearward from the center of a rear end of the outer fitting portion 341; and a connector portion 343 formed rearward of the separator insertion portion 342. The connector portion 343 is crimped to hold a core wire of the sensor output lead 319b and establish electrical connection between the outer terminal member 340 and the sensor output lead 319b. The separator insertion portion 342 is inserted in the separator 318 so as to retain the outer terminal member 340 in the retaining hole 318d of the separator 318 by elastic contact of a separator contact protrusion 342d of the separator insertion portion 342 with the retaining hole 318d. The outer fitting portion 341 is formed such that a diameter of a circle inscribed in a radial cross section of the outer fitting portion 341 is smaller than a diameter of the outer circumferential surface of the rear end part of the oxygen detection element 320. In a state that the outer terminal member 340 is fixed to the oxygen detection element 320, the outer fitting portion 341 is urged by its elastic force into contact with and pressed against the outer electrode layer of the oxygen detection element 320 so as to maintain electrical conduction between the outer terminal member 340 and the outer electrode layer of the oxygen detection element 320. An electromotive force generated in the outer electrode layer is accordingly taken out to the outside through the outer fitting portion 341 and the sensor output lead 319b.

The inner terminal member 330 is made from a stainless steel plate, and includes: an inner fitting portion 333 substantially horseshoe-shaped in cross section in the direction perpendicular to the axis AX; a separator insertion portion 332 extending rearward from the center of a rear end of the inner fitting portion 333; and a connector portion 331 formed rearward of the separator insertion portion 332. The connector portion 331 is crimped to hold a core wire of the sensor output lead 319 and establish electrical connection between the inner terminal member 330 and the sensor output lead 319. The separator insertion portion 332 is inserted in the separator 318 so as to retain the inner terminal member 330 in the retaining hole 318d of the separator 318 by elastic contact of a separator contact protrusion 332d of the separator contact portion 332 with the retaining hole 318d. The inner fitting portion 333 has a heater contact protrusion 336 protruding frontward therefrom. The heater contact protrusion 336 is generally in the shape of a quarter of a circular arc when viewed in the direction of the axis AX. In a state that the inner terminal member 330 is fixed to the oxygen detection element 320, the inner fitting portion 333 (heater contact protrusion 336) is pushed against the ceramic heater 300 so as to bring a side surface of the ceramic heater 300 into contact with the inner circumferential surface of the oxygen detection element 320. Further, the inner fitting portion 333 is formed such that a diameter of a circle circumscribed on a radial cross section of the inner fitting portion 333 is larger than a diameter of the inner circumferential surface of the rear end part of the oxygen detection element 320. In the state that the inner terminal member 330 is fixed to the oxygen detection element 320, the inner fitting portion 333 is urged by its elastic force into contact with and pressed against the inner electrode layer of the oxygen detection element 320 so as to maintain electrical connection between the inner terminal member 330 and the inner electrode layer of the oxygen detection element 320. An electromotive force generated in the inner electrode layer is accordingly taken out to the outside through the insertion portion 341 and the sensor output lead 319.

The ceramic heater 300 is arranged in the inner space G of the oxygen detection element 320 and held in position by the inner terminal member 330, as shown in FIG. 5, so as to heat the oxygen detection element 320 (more specifically, inner circumferential surface of the solid electrolyte body 321) upon the supply of power thereto through the heater leads 312b and 312c.

Figure 6:
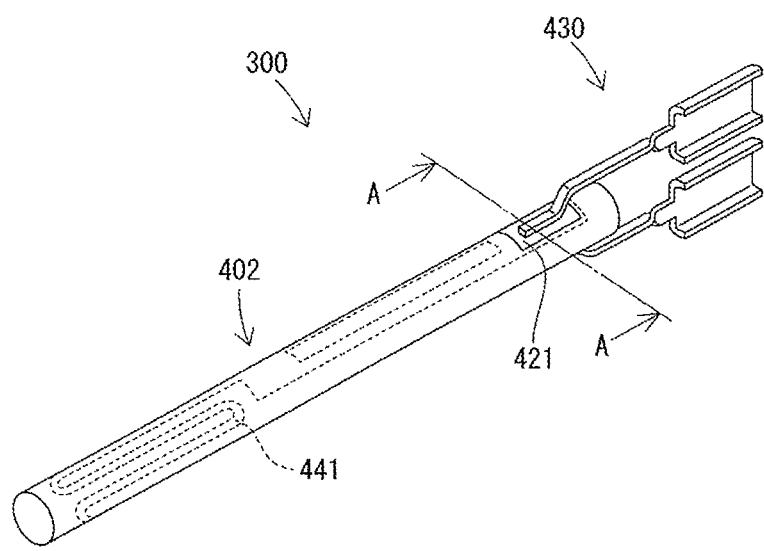
FIG. 6 is a perspective view of the ceramic heater according to the second embodiment of the present invention.
Figure 7:
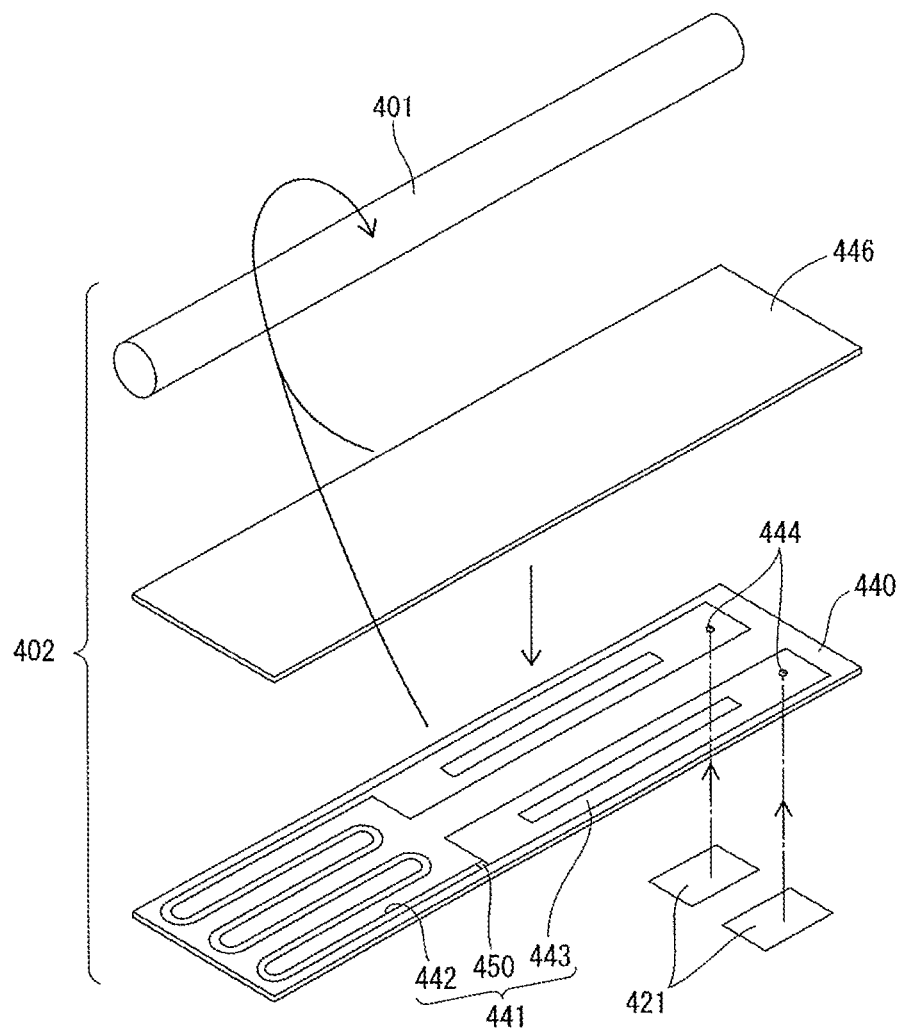
FIG. 7 is an exploded perspective view of the ceramic heater according to the second embodiment of the present invention.
Figure 8:
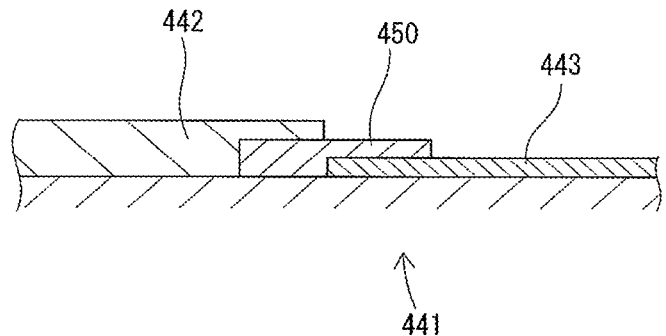
FIG. 8 is a cross-sectional view of a heating resistor of the ceramic heater according to the second embodiment of the present invention.

As shown in FIGS. 6 and 7, the ceramic heater 300 has a round rod shape (substantially circular column shape), and includes a ceramic substrate 402, a heating resistor 441, electrode pads 421 and terminal members 430.

The ceramic substrate 402 includes a round rod-shaped alumina ceramic substrate base 401 and high-insulating alumina ceramic layers 440 and 446 wrapped around the substrate base 401.

The heating resistor 441 is provided as a heater pattern on the alumina ceramic layer 440, and includes a heating portion 442 and a pair of lead portions 443 respectively connected to both ends of the heating portion 442 via joints 450 and each extending in the longitudinal direction of the ceramic heater 300 (that is, the direction of the axis AX). Herein, the heating portion 442 corresponds to the claimed heating portion; the lead portion 443 corresponds to the claimed lead; the joint 450 corresponds to the claimed connection joint (component region).

Two through holes 444 are formed in a rear end part of the alumina ceramic layer 440 so that the lead portions 443 are electrically connected through these through holes 444 to the respective electrode pads 421 on the outer surface of the ceramic heater 300. The heater leads 312b and 312c are respectively electrically connected to the electrode pads 421 by the terminal members 430.

The heating portion 442 is made of a material containing a first metal as a predominant component; whereas the lead portions 443 are each made of a material containing a second metal as a predominant component. In the second embodiment, the first metal is platinum (Pt); and the second metal is palladium (Pd).

A production method of the ceramic heater 300 will be next will be explained below. Herein, green sheets for formation of the alumina ceramic layers 440 and 446 are referred to as "green sheets 440 and 446" for the sake of convenience.

After that, a Pd-containing paste for formation of the lead portions 443 is prepared and screen printed on the green sheet 440. A Pd/Pt-containing paste for formation of the joint 450 is prepared and screen printed over an end part of the printed Pd-containing paste. A Pt-containing paste for formation of the heating portion 442 is prepared and screen printed on the green sheet 440 so as to overlap a part of the printed Pd/Pt-containing paste. The green sheet 446 is press-bonded at one surface thereof to the paste-printed surface of the green sheet 440. A paste containing alumina is applied to the other surface of the green sheet 446.

The resulting laminate of the green sheets 440 and 446 is wrapped around the substrate base 401 with the alumina paste-applied surface of the green sheet 446 facing inward, and is pressed inward from the outer circumference side.

The thus-formed green heater assembly is fired, thereby obtaining the ceramic heater 300.

The joint 450 between the heating portion 442 and the lead portion 443 as the characteristic configuration of the second embodiment will be now explained in detail below.

In the second embodiment, the joint 450 contains Pt (as the first metal) and Pd (as the second metal) in a total amount of 50 mass % or more. The amount of Pt contained in the joint 450 ranges between the amount of Pt contained in the heating portion 442 and the amount of Pt contained in the lead portion 443. Namely, the concentration of Pt in the joint 450 is lower than the concentration of Pt in the heating portion 442 and higher than the concentration of Pt in the lead portion 443. Further, the amount of Pd contained in the joint 450 ranges between the amount of Pd contained in the heating portion 442 and the amount of Pd contained in the lead portion 443. Namely, the concentration of Pd in the joint 450 is lower than the concentration of Pd in the lead portion 443 and higher than the concentration of Pd in the heating portion 442. The joint 450 has a Pt concentration value between those of the heating portion 442 and the lead portion 443 and has a Pd concentration value between those of the heating portion 442 and the lead portion 443.

The amount of Pt in the joint 450 is preferably 30 to 70 mass %, more preferably 40 to 60 mass %, still more preferably 45 to 55 mass %, based on 100 mass % of the total amount of Pt and Pd in the joint 450.

The amount of Pd in the joint 450 is preferably 30 to 70 mass %, more preferably 40 to 60 mass %, still more preferably 45 to 55 mass %, based on 100 mass % of the total amount of Pt and Pd in the joint 450.

It is preferable that metal components of the joint 450 substantially consist of Pt and Pd. The expression "substantially consist of Pt and Pd" means that the amount of any metal component other than Pt and Pd is substantially 0% (more specifically, less than 5.0 mass %).

In the ceramic heater 300, the joint 450 is provided to relieve the abrupt metal concentration gradient between the heating portion 442 and the lead portion 443. It is thus unlikely that Pd as the predominant component of the lead portion 443 will migrate to the heating portion 442 during the firing (heat treatment) step. It is consequently possible to prevent the occurrence of voids in the lead portion 443 due to the migration of Pd and thereby possible to suppress a break in the lead portion 443.

In the case of using Pt as the first metal in combination with Pd as the second metal, there is a high tendency that the migration of Pd will take place during the firing step. Such metal migration is however effectively prevented by the joint 450.

Third Embodiment

A multi-gas sensor apparatus 1 with an ammonia sensor unit 21 according to the third embodiment of the present invention will be described below with reference to FIGS. 1, 2 and 9 to 10.

The multi-gas sensor apparatus 1 according to the third embodiment is structurally similar to that according to the first embodiment, except for the configuration of the ammonia sensor unit 21. In the third embodiment, the same parts and portions as those in the first embodiment are designated by the same reference numerals; and detailed explanations thereof will be omitted.

In the third embodiment, the multi-gas sensor apparatus 1 includes a multi-gas sensor 2 and a sensor controller 3 (see FIGS. 1 and 2) as in the first embodiment. As the configuration of the sensor controller 3 in the third embodiment is similar to that in the first embodiment, a detailed explanation of the sensor controller 3 will be omitted herefrom.

The multi-gas sensor 2 is provided with a sensor element assembly 10, a metal shell 110, a separator 134 and connection terminals 138 as shown in FIG. 1. The sensor element assembly 10 has a NOx sensor unit 11 (as a NOx detection element) and an ammonia sensor unit 21. In the third embodiment, the ammonia sensor unit 21 corresponds to the claimed gas sensor element.

A detailed explanation of the NOx sensor unit 11 will be omitted as the structure of the NOx sensor unit 11 in the first embodiment is similar to that in the first embodiment.

Figure 9:
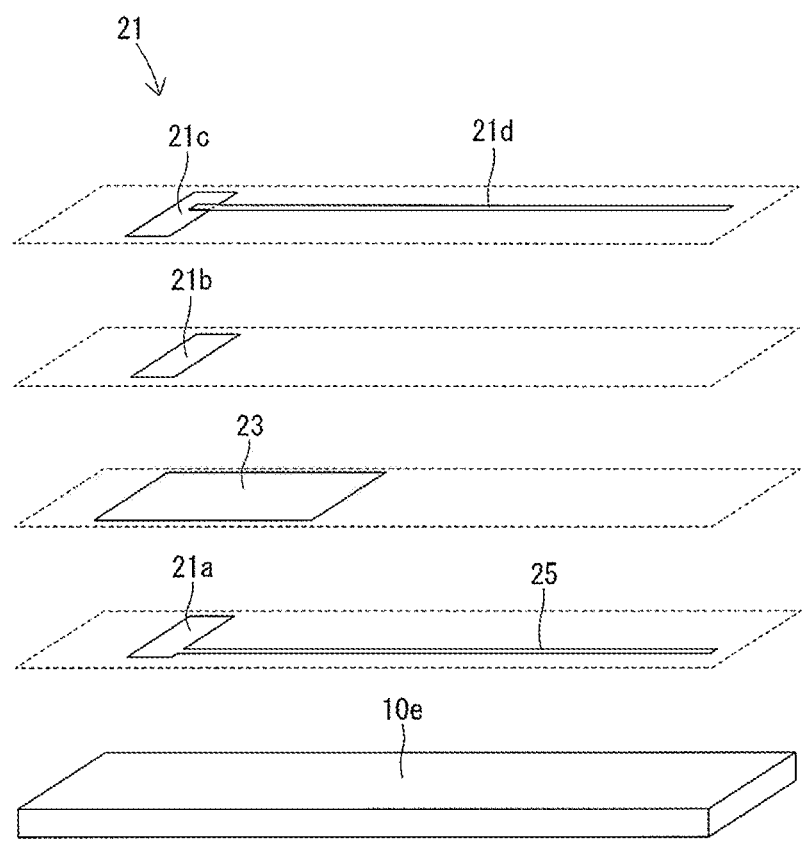
FIG. 9 is an exploded perspective view of an ammonia sensor unit of a multi-gas sensor according to a third embodiment of the present invention.

As shown in FIGS. 2 and 9, the ammonia sensor unit 21 is of the mixed potential type having: a reference electrode 21a containing platinum as a predominant component; a solid electrolyte body 23 containing zirconia as a predominant component; an intermediate layer 21b (as an electrode) containing cobalt oxide and zirconia as predominant components; and an ammonia detection electrode 21c containing gold (Au) as a predominant component. Herein, the ammonia detection electrode 21c corresponds to the claimed electrode; the ammonia detection electrode lead 21d corresponds to the claimed lead; the reference electrode 21a corresponds to the claimed second electrode; and the solid electrolyte body 23 corresponds to the claimed solid electrolyte body. The ammonia sensor unit 21 is integrally covered with a protection layer 24 of porous material.

Figure 10:
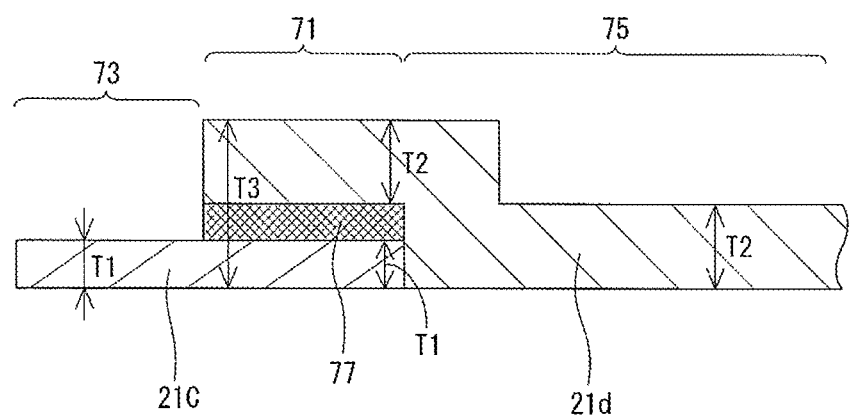
FIG. 10 is a cross-sectional view of the connection between an ammonia sensor electrode and an electrode lead in the ammonia sensor unit of the multi-gas sensor according to the third embodiment of the present invention.

An ammonia detection electrode lead 21d containing platinum (Pt) as a predominant component is connected to the ammonia detection electrode 21c and arranged to extend rearward from the ammonia detection electrode 21c in the direction of the axis O. In the third embodiment, the ammonia detection electrode 21c and the ammonia detection electrode lead 21d are directly electrically connected to each other as shown in FIG. 10. A detailed explanation of the connection structure between the ammonia detection electrode 21c and the ammonia detection electrode lead 21d will be given later.

A production method of the sensor element assembly 10 with the NOx sensor unit 11 and the ammonia sensor unit 21 will be next explained below. As the NOx sensor unit 11 can be produced by a known method, a detail explanation of the production method of the NOx sensor unit 11 will be omitted herefrom. On the other hand, the ammonia sensor unit 21 can be produced by the following method.

First prepared is a paste containing Pt as the predominant component of the reference electrode 21a, an alumina binder (as a common inorganic oxide base material) and an organic solvent. The prepared paste (hereinafter referred to as "Pt-containing paste") is screen printed on the insulating layer 10e and fired at a predetermined temperature (e.g. about 1400° C. or higher). Further, a paste is prepared containing a powder of oxide as the predominant component of the solid electrolyte body 23, a binder and an organic solvent. The prepared solid electrolyte paste is screen printed on the fired reference electrode 21a and fired at a predetermined temperature (e.g. 1500° C.). Thus formed are the reference electrode 21a and the solid electrolyte body 23.

The intermediate layer 21b is formed on the solid electrolyte body 23 by preparing a paste containing the first metal oxide and solid electrolyte material as the components of the intermediate layer 21b, screen printing the prepared paste on the solid electrolyte body 23 and firing the printed paste at a predetermined temperature (e.g. 1000° C.).

After that, an Au-containing paste for formation of the ammonia detection electrode 21c is prepared and screen printed on the intermediate layer 21b. A Pt-containing paste for formation of the ammonia detection electrode lead 21d is prepared and screen printed on the intermediate layer 21 so as to overlap an part of the printed Au-containing paste. These overlappingly printed pastes are fired at a predetermined temperature (e.g. 1000° C.), thereby forming the ammonia detection electrode 21c in electrical connection with the ammonia detection electrode lead 21d. Finally, the protection layer 24 is formed by preparing a paste containing alumina etc., screen printing the prepared paste over the reference electrode 21a, the solid electrolyte body 23, the intermediate layer 21b and the ammonia detection electrode 21c, and then, firing the printed paste at a predetermined temperature (e.g. 1000° C.). With this, the ammonia sensor unit 21 is completed.

The connection structure between the ammonia detection electrode 21c and the ammonia detection electrode lead 21d as the characteristic configuration of the third embodiment will be now explained in detailed below.

As shown in FIG. 10, the connection structure includes: an individual electrode section 73 in which the ammonia detection electrode 21c is individually present without being overlapped by the ammonia detection electrode lead 21d; a connection section 71 in which the ammonia detection electrode 21c and the ammonia detection electrode lead 21d overlap each other in a thickness direction thereof; and an individual lead section 75 in which the ammonia detection electrode lead 21d is individually present without overlapping the ammonia detection electrode 21c. In the third embodiment, the ammonia detection electrode lead 21d is disposed on and overlaps the ammonia detection electrode 21c in the connection section 71.

The first metal contained as the predominant component (noble metal element) of the individual electrode section 73 is lower in specific gravity than the second metal contained as the predominant component (noble metal component) of the individual lead section 75. As mentioned above, the first metal is Au; and the second metal is Pt in the third embodiment.

As shown in FIG. 10, a thickness T3 of the connection section 71 is larger than the sum of a thickness T1 of the individual electrode section 73 and a thickness T2 of the individual lead section 75 (T3>T1+T2).

When the connection section 71 is observed in cross section, a boundary zone 77 of the ammonia detection electrode 21c and the ammonia detection electrode lead 21d is formed as a part of the connection section 71 excluding an outer (top) surface part of the connection section 71 by an amount of the thickness T2 of the individual lead section 75 and excluding an inner (bottom) surface part of the connection section 71 by an amount of the thickness T1 of the individual electrode section 73 as shown by cross hatching in FIG. 10. This boundary zone 77 to the claimed connection boundary (component region). Herein, the expression "the connection section 71 is observed in cross section" means that "a cross section of the ammonia sensor unit 21 taken through the ammonia detection electrode 21c in the axis direction is observed from the thickness direction".

The amount of Au contained in the boundary zone 77 ranges between the amount of Au contained in the individual electrode section 73 (i.e. in the ammonia detection electrode 21c) and the amount of Au contained in the individual lead section 75 (i.e. in the ammonia detection electrode lead 21d). Namely, the concentration of Au in the boundary zone 77 is lower than the concentration of Au in the individual electrode section 73 and higher than the concentration of Au in the individual lead section 75.

The thickness T1 of the individual electrode section 73 is not particularly limited. In order to ensure ammonia gas detection accuracy, the thickness T1 of the individual electrode section 73 is preferably in the range of 5 μm to 40 μm, more preferably 10 μm to 30 μm, still more preferably 15 μm to 25 μm.

The thickness 12 of the individual lead section 75 is not particularly limited. In order to ensure high conductivity and to reduce the amount of expensive noble metal used, the thickness T2 of the individual lead section 75 is preferably in the range of 5 μm to 40 μm, more preferably 10 μm to 30 μm, still more preferably 15 μm to 25 μm. In the third embodiment, the thickness T2 of the individual lead section 75 refers to the thickness of any part of the individual lead section 75 other than a thickened part (in FIG. 10, left-side end part) thereof adjacent to the connection section 71.

The thickness of the boundary zone 77, which is equal to a subtraction of the thickness T1 of the individual electrode section 73 and the thickness T2 of the individual lead section 75 from the thickness T3 of the connection section 71, is not also particularly limited. In order to effectively suppress a break and to reduce the amount of expensive noble metal used, the thickness of the boundary zone 77 is preferably in the range of 1 μm to 40 μm, more preferably 5 μm to 30 μm, still more preferably 10 μm to 20 μm.

Each of these thickness values indicates an average value of three thickness measurement results obtained by e.g. SEM observation at a magnification of 300 times.

A formation method of the connection structure in the third embodiment will be explained in more detail.

When the Au-containing paste for formation of the ammonia detection electrode 21c is screen printed, the thickness of the Au-containing paste applied in the connection section 71 is increased to a larger value than that in the individual electrode section 73. The boundary zone 77 is formed by the amount of increase of the Au-containing paste during the firing. The amount of Au in the boundary zone 77 however becomes smaller than the amount of Au in the individual electrode section 73 because Au of the Au-containing paste for formation of the boundary zone 77 migrates to the Pt-containing paste for formation of the ammonia detection electrode lead 21d during the firing.

Each of the amounts of Au contained in the individual electrode section 73, the individual lead section 75 and the boundary zone 77 relative to all metal components (noble metal components) is determined as the average value of results of elementary analysis performed by an electron probe micro analyzer (EPMA) at a plurality of points on the cross section of each section 73, 75, 77.

The amount of Au contained relative to all metal components (noble metal components) in the individual electrode section 73 is preferably 70 mass % or more, more preferably 80 mass % or more, still more preferably 86 mass % or more. The upper limit amount of Au contained in the individual electrode section 73 may be 100 mass %. Since Au is contained as the predominant component in the individual electrode section 73, the individual electrode section 73 ensures its function as a collector.

As in the case of the first embodiment, the individual electrode section 73 (i.e. the ammonia detection electrode 21c) may or may not contain an oxide of at least one kind of metal selected from the group consisting of cobalt (Co), manganese (Mn), copper (Cu), nickel (Ni) and cerium (Ce) as a first metal oxide. When the first metal oxide is not contained in the individual electrode section 73, combustion of ammonia gas on the individual electrode section 73 can be suppressed so that the amount of ammonia gas reaching the interface between the individual electrode section 73 and the intermediate layer 21b becomes unlikely to unlikely to decrease. In other words, the detection accuracy of the ammonia sensor unit 21 can be improved so as to enable accurate detection of low-concentration ammonia (e.g. of the order of 10 ppm).

Further, it is preferable that the individual electrode section 73 is porous, containing, as a second metal oxide, an oxide of at least one kind of metal selected from the group consisting of zirconium (Zr), yttrium (Y), aluminum (Al) and silicon (Si) in order to impart gas permeability to the individual electrode section 73. In this case, ammonia gas easily passes through the individual electrode section 73 and reaches the interface between the individual electrode section 73 and the intermediate layer 21b. The amount of the second metal oxide contained in the individual electrode section 73 is preferably in the range of 5 mass % to 30 mass % based on 100 mass % of the total amount of the individual electrode section 73.

The amount of Au contained relative to all metal components (noble metal components) in the individual lead section 75 is smaller than that in the individual electrode section 73.

The amount of Pt contained relative to all metal components (noble metal components) in the individual lead section 75 is preferably 50 mass % or more, more preferably 70 mass % or more, still more preferably 90 mass % or more.

The amount of Au contained relative to all metal components (noble metal components) in the boundary zone 77 is larger than that in the individual lead section 75. As mentioned above, the amount of Au contained relative to all metal components (noble metal components) in the boundary zone 77 is generally smaller than that in the individual electrode section 73.

In the third embodiment, the boundary zone 77 is provided between the electrode function part and lead function part of the connection section 71 so that migration of Au is limited to within the boundary zone 77. It is consequently possible to prevent the migration of Au from the electrode function part to the lead function part and thereby possible suppress a break in the connection section 71.

Fourth Embodiment

A multi-gas sensor according to the fourth embodiment of the present invention will be described below with reference to FIG. 11.

The multi-gas sensor according to the fourth embodiment is structurally similar to the multi-gas sensor 1 according to the third embodiment, except for the connection structure between the ammonia detection electrode 21c and the ammonia detection electrode lead 21d. In the fourth embodiment, the same parts and portions as those in the third embodiment are designated by the same reference numerals; and detailed explanations thereof will be omitted.

Figure 11:
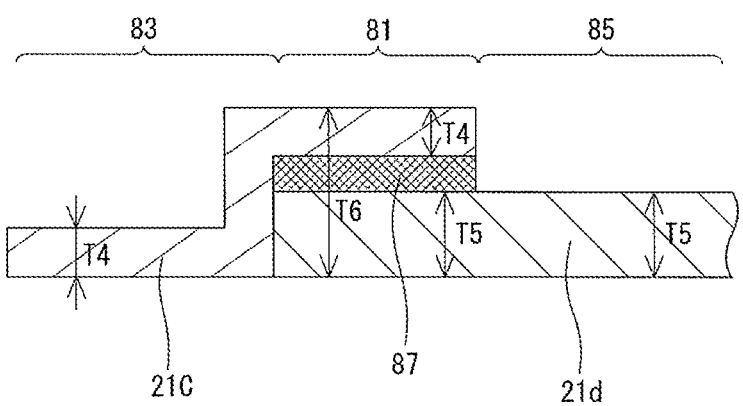
FIG. 11 is a cross-sectional view of the connection between an ammonia sensor electrode and an electrode lead in an ammonia sensor unit of a multi-gas sensor according to a fourth embodiment of the present invention.

As shown in FIG. 11, the connection structure includes: an individual electrode section 83 in which the ammonia detection electrode 21c is individually present without overlapping the ammonia detection electrode lead 21d; a connection section 81 in which the ammonia detection electrode 21c and the ammonia detection electrode lead 21d overlap each other in a thickness direction thereof; and an individual lead section 85 in which the ammonia detection electrode lead 21d is individually present without being overlapped by the ammonia detection electrode 21c. In the fourth embodiment, the ammonia detection electrode 21c is disposed on and overlaps the ammonia detection electrode lead 21d in the connection section 81. By this connection structure, the ammonia detection electrode 21c and the ammonia detection electrode lead 21d are directly connected to each other.

The first metal contained as the predominant component (noble metal element) of the individual electrode section 83 is lower in specific gravity than the second metal contained as the predominant component (noble metal component) of the individual lead section 85. As in the third embodiment, gold (Au) and platinum (Pt) are respectively used as the first and second metals in the fourth embodiment.

Further, a thickness T6 of the connection section 81 is larger than the sum of a thickness T4 of the individual electrode section 83 and a thickness T5 of the individual lead section 85 (T6>T4+T5) as shown in FIG. 11 in the fourth embodiment as in the third embodiment.

When the connection section 81 is observed in cross section, a boundary zone 87 of the ammonia detection electrode 21c and the ammonia detection electrode lead 21d is formed as a part of the connection section 81 excluding an outer (top) surface part of the connection section 81 by an amount of the thickness T4 of the individual electrode section 83 and excluding an inner (bottom) surface part of the connection section 81 by an amount of the thickness T5 of the individual lead section 85 as shown by cross hatching in FIG. 11. This boundary zone 87 corresponds to the claimed connection boundary (component region). Herein, the expression "the connection section 81 is observed in cross section" means that "a cross section of the ammonia sensor unit 21 taken through the ammonia detection electrode 21c in the axis direction is observed from the thickness direction".

The thickness T4 of the individual electrode section 83 is not particularly limited. In order to ensure ammonia gas detection accuracy, the thickness T4 of the individual electrode section 83 is preferably in the range of 5 μm to 40 μm, more preferably 10 μm to 30 μm, still more preferably 15 μm to 25 μm. Herein, the thickness T4 of the individual electrode portion 83 refers to the thickness of any part of the individual electrode portion 83 other than a thickened part (in FIG. 11, right-side end part) thereof adjacent to the connection section 81.

The thickness T5 of the individual lead section 85 is not particularly limited. In order to ensure high conductivity and to reduce the amount of expensive noble metal used, the thickness T5 of the individual lead section 85 is preferably in the range of 5 μm to 40 μm, more preferably 10 μm to 30 μm, still more preferably 15 μm to 25 μm.

The thickness of the boundary zone 87, which is equal to a subtraction of the thickness T4 of the individual electrode section 83 and the thickness T5 of the individual lead section 85 from the thickness T6 of the connection section 81 is not also particularly limited. In order to effectively present the occurrence of a break and to reduce the amount of expensive noble metal used, the thickness of the boundary zone 87 is preferably in the range of 1 μm to 40 μm, more preferably 5 μm to 30 μm, still more preferably 10 μm to 20 μm.

A formation method of the connection structure in the fourth embodiment will be explained below.

The ammonia sensor unit 21 can be produced by the same method as explained above in the third embodiment, except that the Au-containing paste for formation of the ammonia detection electrode 21c is screen printed after the Pt-containing paste for formation of the ammonia detection electrode lead 21d.

When the Au-containing paste for formation of the ammonia detection electrode 21c is screen printed, the thickness of the Au-containing paste applied in the connection section 81 is increased to a larger value than that in the individual electrode section 83. During the firing, the boundary zone 87 is formed by the amount of increase of the Au-containing paste. The amount of Au in the boundary zone 87 becomes smaller than the amount of Au in the individual electrode section 83 because Au of the Au-containing paste for formation of the boundary zone 87 migrates to the Pt-containing paste for formation of the ammonia detection electrode lead 21d during the firing.

Each of the amounts of Au contained in the individual electrode section 83, the individual lead section 85 and the boundary zone 87 relative to all metal components (noble metal components) is determined as the average value of results of elementary analysis performed by an electron probe micro analyzer (EPMA) at a plurality of points on the cross section of each section 83, 85, 87.

The amount of Au contained relative to all metal components (noble metal components) in the individual electrode section 83 is preferably 70 mass % or more, more preferably 80 mass % or more, still more preferably 86 mass % or more. The upper limit amount of Au contained in the individual electrode section 83 may be 100 mass %. Since Au is contained as the predominant component in the individual electrode section 83, the individual electrode section 83 ensures its function as a collector.

As in the case of the third embodiment, the individual electrode section 83 may or may not contain an oxide of at least one kind of metal selected from the group consisting of cobalt (Co), manganese (Mn), copper (Cu), nickel (Ni) and cerium (Ce) as a first metal oxide. When the first metal oxide is not contained in the individual electrode section 83, combustion of ammonia gas on the individual electrode section 83 can be suppressed so that the amount of ammonia gas reaching the interface between the individual electrode section 83 and the intermediate layer 21b becomes unlikely to unlikely to decrease. In other words, the detection accuracy of the ammonia sensor unit 21 can be improved so as to enable accurate detection of low-concentration ammonia (e.g. of the order of 10 ppm).

Further, it is preferable that the individual electrode section 83 is porous, containing, as a second metal oxide, an oxide of at least one kind of metal selected from the group consisting of zirconium (Zr), yttrium (Y), aluminum (Al) and silicon (Si) in order to impart gas permeability to the individual electrode section 83. In this case, ammonia gas easily passes through the individual electrode section 83 and reaches the interface between the individual electrode section 83 and the intermediate layer 21b. The amount of the second metal oxide contained in the individual electrode section 83 is preferably in the range of 5 mass % to 30 mass % based on 100 mass % of the total amount of the individual electrode section 83.

The amount of Au contained relative to all metal components (noble metal components) in the individual lead section 85 is smaller than that in the individual electrode section 83.

The amount of Pt contained relative to all metal components (noble metal components) in the individual lead section 85 is preferably 50 mass % or more, more preferably 70 mass % or more, still more preferably 90 mass % or more.

The amount of Au contained relative to all metal components (noble metal components) in the boundary zone 87 is larger than that in the individual lead section 85. As mentioned above, the amount of Au contained relative to all metal components (noble metal components) in the boundary zone 87 is generally smaller than that in the individual electrode section 83.

In the fourth embodiment, the boundary zone 87 is provided between the electrode function part and lead function part of the connection section 81 so that migration of Au is limited to within the boundary zone 87. It is consequently possible to prevent the migration of Au from the electrode function part to the lead function part and thereby possible suppress a break in the connection section 81.

EXAMPLES

The present invention will be described in more detail below by way of the following examples.

1. Production of Samples

Figure 4:
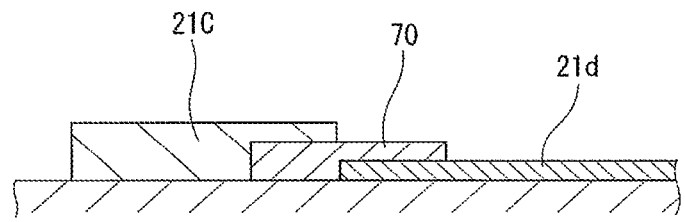
FIG. 4 is a cross-sectional view of an ammonia sensor electrode of the ammonia sensor unit of the multi-gas sensor according to the first embodiment of the present invention.

Samples of Examples were produced in each of which an electrode was connected to a lead via a joint as in the first embodiment (FIG. 4).

A Pt-containing paste for formation of the electrode was prepared containing Pt, Au, ethyl cellulose, butyl carbitol and zirconia such that the composition ratio of Pt/Au became 14/86 (mass %) after the firing. A Pd-containing paste for formation of the electrode was prepared containing Pd, Au, ethyl cellulose, butyl carbitol and zirconia such that the composition ratio of Pd/Au became 7/93 (mass %) after the firing.

A paste for formation of the lead was prepared containing Pt, ethyl cellulose, butyl carbitol and zirconia such that the composition ratio of Pt became 100 (mass %).

Further, three kinds of pastes for formation of the joint were prepared containing Pt, Au, ethyl cellulose, butyl carbitol and zirconia such that the composition ratio of Pt/Au became 70/30, 43/57 or 30/70 (mass %).

In each Example, the above-prepared lead-forming paste was screen printed on an alumina substrate. The above-prepared joint-forming paste was screen printed over an end part of the printed lead forming paste. The above-prepared electrode-forming paste was screen printed on the alumina substrate so as to overlap a part of the printed joint-forming paste. These overlappingly printed pastes on the alumina substrate were fired at a predetermined temperature (1100° C.).

Accordingly, there were obtained total six kinds of samples with varying combinations of two types of electrodes and three types of joints.

For comparison purposes, a sample of Comparative Example was produced in which an electrode and a lead were directly connected to each other without a joint.

In Comparative Example, the above-prepared Pt-containing electrode-forming and the above-prepared lead-forming paste were used. The lead-forming paste was screen printed on an alumina substrate. Then, the Pt-containing electrode-forming paste was screen printed on the alumina substrate so as to overlap an end part of the printed lead-forming paste. These overlappingly printed pastes on the alumina substrate were fired at a predetermined temperature (1100° C.).

2. Evaluation

In Comparative Example, a part of the electrode in direct contact with the lead was observed. The observed electrode part was seen in whitish color because zirconia (in white color) was more recognizable due to migration of Au of the electrode to the lead. The color of this observed electrode part of Comparative Example was set as a reference color.

In each of Examples, on the other hand, a part of the electrode in contact with the joint was observed. When the amount of Au migrating from the electrode in Example was smaller than that in Comparative Example, the white color of zirconia was less recognizable whereby the observed electrode part was seen in color darker than the reference color. When the amount of Au migrating from the electrode in Example was equivalent to or larger than that in Comparative Example, the white color of zirconia was more recognizable whereby the observed electrode part was seen in color equivalent to or lighter than the reference color. In view of these facts, the sample was evaluated as: "good" when the color of the observed electrode part was darker than the reference color, and "not good" when the color of the observed electrode part was lighter than or equivalent to the reference color.

3. Evaluation Results

The evaluation results are shown in TABLE 1.

TABLE 1

| | Example (sample with joint) Pt/Au ratio (mass %) | | | Comparative Example |
|---|---|---|---|---|
| | 70/30 | 43/57 | 30/70 | (sample with no joint) |
| Pt electrode | good | good | good | ref. |
| Pd electrode | good | good | good | — |

In each of Examples where the electrode and the lead were connected via the joint, the abrupt metal concentration gradient was relieved by the joint. As the migration of Au from the electrode to the lead was suppressed, zirconia was less recognizable in the electrode. The observed electrode part was thus seen in darker color than the reference electrode.

Modification Examples

Although the present invention has been described with reference to the above embodiments, the above embodiments are intended to facilitate understanding of the present invention and are not intended to limit the present invention thereto. Various changes and modifications can be made to the above embodiments without departing from the scope of the present invention.

(1) In the above first to fourth embodiments, the gas sensor element is embodied as the ammonia sensor element or oxygen sensor element. The present invention is however not limited to those sensor elements, and is applicable to various types of gas sensor elements.

(2) The above first, third and fourth embodiments specifically refer to the combination of Au as the first metal and Pt as the second metal; and the above second embodiment specifically refers to the combination of Pt as the first metal and Pd as the second metal. The combination of the first and second metals is however not limited to those of the above embodiments. The first and second metals can be metals of different specific gravities. For example, gold (Au), platinum (Pt), rhodium (Rh) and the like are suitably usable as the predominant component of the electrode; platinum (Pt), palladium (Pd), tungsten (W), rhodium (Rh) or the like are suitably usable as the predominant component of the heating portion; and palladium (Pd), platinum (Pt) and the like are suitably usable as the predominant component of the lead. Among others, the present invention is also suitably applicable to the combination of Au as the first metal and Pd as the second metal, the combination of Rh as the first metal and Pt as the second metal or the like.

(3) In the above second embodiment, the heater is embodied as the ceramic heater for heating the bottomed cylindrical-shape oxygen sensor element. The present invention is however not limited to such a heater, and is applicable to e.g. the heater 19 of the above first embodiment and any other types of heaters.

(4) Although the heating portion 442 and the lead portion 443 are connected indirectly via the joint 450 in the above embodiment in the above second embodiment, the heating portion 442 and the lead portion 443 may be alternatively directly connected to each other.

For example, the connection structure between the ammonia detection electrode 21c and the ammonia detection electrode lead 21d in the above fourth embodiment (FIG. 11) may be adopted for connection of the heating portion 442 and the lead portion 443. In this case, the connection structure includes: an individual heating section in which the heating portion 442 is individually present without overlapping the lead portion 443; a connection section in which the heating portion 442 is disposed on and overlaps the lead portion 443 in the thickness direction; and an individual lead section in which the lead portion 443 is individually present without being overlapped by the heating portion 442 although not specifically shown in the drawings. When the connection section is observed in cross section, a boundary zone of the heating portion 442 and the lead portion 443 is provided as a part of the connection section excluding an outer (top) surface part of the connection section by an amount of the thickness of the individual heating section and excluding an inner (bottom) surface part of the connection section by an amount of the thickness of the individual lead section. The amount of Pt (as the first metal) contained relative to all metal components (noble metal components) in the boundary zone ranges between those in the individual heating section and the individual lead section. Namely, the concentration of Pt in the boundary zone is lower than the concentration of Pt in the individual heating section and higher than the concentration of Pt in the individual lead section.

The lead portion 443 may alternatively be disposed on and overlap the heating portion 442 in the connection section as in the above third embodiment (FIG. 10). Even in this connection structure, a boundary zone of the heating portion 442 and the lead portion 443 is provided as a part of the connection section excluding an outer (top) surface part of the connections section by an amount of the thickness of the individual lead section and excluding an inner (bottom) surface part of the connection section by an amount of the thickness of the individual heating section.

The entire contents of Japanese Patent Application No. 2018-059397 (filed on Mar. 27, 2018), No. 2018-081191 (filed on Apr. 20, 2018) and No. 2019-001248 (filed on Jan. 8, 2019) are herein incorporated by reference. The scope of the present invention is defined with reference to the following claims.

What is claimed is:

1. A gas sensor element, comprising:
   an electrode containing a first metal as a predominant component; and
   a lead containing a second metal as a predominant component,
   the electrode and the lead being connected to each other indirectly via a connection joint,
   wherein the connection joint includes a component region in which either one of the first and second metals lower in specific gravity than the other of the first and second metals is contained in an amount ranging between an amount of the one of the first and second metals contained in the electrode and an amount of the one of the first and second metals contained in the lead, and
   wherein the other of the first and second metals is contained in the component region in an amount ranging between an amount of the other of the first and second metals contained in the electrode and an amount of the other of the first and second metals contained in the lead.

2. The gas sensor element according to claim 1, further comprising:
   a second electrode different from the electrode; and
   a solid electrolyte body arranged between the electrode and the second electrode,
   wherein the second electrode contains the second metal as a predominant component, and
   wherein the gas sensor element is configured as a mixed-potential-type sensor element.

3. The gas sensor element according to claim 1,
   wherein metal elements of the connection joint substantially consist of the first and second metals.

4. The gas sensor element according to claim 1,
   wherein the connection joint contains 30 to 70 mass % of the first metal and 30 to 70 mass % of the second metal based on 100 mass % of the total amount of the first and second metals.

5. The gas sensor element according to claim 1,
   wherein the specific gravity of the first metal is lower than the specific gravity of the second metal.

6. The gas sensor element according to claim 1,
   wherein the first metal is gold, and
   wherein the second metal is platinum.

7. The gas sensor element according to claim 1,
   wherein the gas sensor element is configured to measure a concentration of ammonia in a gas under measurement.

8. A gas sensor comprising the gas sensor element according to claim 1.

9. A heater, comprising:
   a heating portion containing a first metal as a predominant component; and
   a lead containing a second metal as a predominant component,
   the heating portion and the lead being connected to each other directly or indirectly via a connection joint,
   wherein, when the heating portion and the lead are directly connected to each other, a connection boundary of the heating portion and the lead includes a component region in which either one of the first and second metals lower in specific gravity than the other of the first and second metals is contained in an amount ranging between an amount of the one of the first and second metals contained in a part of the heating portion other than the connection boundary and an amount of the one of the first and second metals contained in a part of the lead other than the connection boundary; and
   wherein, when the heating portion and the lead are connected indirectly via the connection joint, the connection joint includes a component region in which either one of the first and second metals lower in specific gravity than the other of the first and second metals is contained in an amount ranging between an amount of the one of the first and second metals contained in the heating portion and an amount of the one of the first and second metals contained in the lead.

10. A gas sensor comprising the heater according to claim 9.

* * * * *